(12) United States Patent
Umemura et al.

(10) Patent No.: US 7,486,777 B2
(45) Date of Patent: Feb. 3, 2009

(54) COOLER, X-RAY TUBE APPARATUS, AND METHOD FOR OPERATING COOLER

(75) Inventors: Tomohide Umemura, Nasushiobara (JP); Yoshiaki Shiratori, Otawara (JP); Takayuki Kitami, Nasushiobara (JP)

(73) Assignees: Kabushiki Kaisha Toshiba, Tokyo (JP); Toshiba Electron Tubes & Devices Co., Ltd., Tochigi-ken (JP)

( * ) Notice: Subject to any disclaimer, the term of this patent is extended or adjusted under 35 U.S.C. 154(b) by 0 days.

(21) Appl. No.: 11/812,465

(22) Filed: Jun. 19, 2007

(65) Prior Publication Data
US 2007/0242803 A1 Oct. 18, 2007

Related U.S. Application Data

(63) Continuation of application No. PCT/JP2006/321584, filed on Oct. 23, 2006.

(30) Foreign Application Priority Data
Oct. 31, 2005 (JP) .............................. 2005-317717

(51) Int. Cl.
*H01J 35/10* (2006.01)
(52) U.S. Cl. ...................................... 378/141; 378/199
(58) Field of Classification Search ................ 378/141, 378/130, 119, 199–200
See application file for complete search history.

(56) References Cited

U.S. PATENT DOCUMENTS 6,623,160 B2 * 9/2003 McCarthy, Jr. .............. 378/200
2002/0146092 A1* 10/2002 Richardson et al. ......... 378/130

FOREIGN PATENT DOCUMENTS

| JP | 03-241699 | 10/1991 |
| JP | 04-141997 | 5/1992 |
| JP | 10-106790 | 4/1998 |
| JP | 2000-164390 | 6/2000 |
| JP | 2001-307668 | 11/2001 |
| JP | 2002-289395 | 10/2002 |

OTHER PUBLICATIONS

International Search Report dated Jan. 30, 2007 for Appln. No. PCT/JP2006/321584 filed Oct. 23, 2006.

* cited by examiner

*Primary Examiner*—Hoon Song
(74) *Attorney, Agent, or Firm*—Pillsbury Winthrop Shaw Pittman, LLP (57) ABSTRACT

A cooler that circulates cooling fluid to cool an X-ray tube, and that comprises a circulation unit that has a first end unit and a second end unit, and an expansion mechanism that has a vessel and a bellows that divides the inside of the vessel into a first chamber and a second chamber, wherein the first end unit and the second end unit are detachably coupled to the X-ray tube and are closed when being uncoupled from the X-ray tube, and the expansion mechanism can be switched between a first state and a second state.

7 Claims, 5 Drawing Sheets

COOLER, X-RAY TUBE APPARATUS, AND METHOD FOR OPERATING COOLER

CROSS REFERENCE TO RELATED APPLICATIONS

This is a Continuation Application of PCT Application No. PCT/JP2006/321584, filed Oct. 23, 2006, which was published under PCT Article 21(2) in English.

This application is based upon and claims the benefit of priority from prior Japanese Patent Application No. 2005-317717, filed Oct. 31, 2005, the entire contents of which are incorporated herein by reference.

BACKGROUND OF THE INVENTION

1. Field of the Invention

The present invention relates to a cooler, an X-ray tube apparatus having the cooler, and a method for operating the cooler.

2. Description of the Related Art

In general, an X-ray tube apparatus such as an X-ray computed tomography (CT) apparatus is used in a medical or industrial diagnosis system. The X-ray tube apparatus has a pedestal, and a revolving body that is rotatably mounted on the pedestal. For example, as is disclosed in Jpn. Pat. Appln. Publication No. 2000-164390, an X-ray tube that radiates X-rays, and a cooler that cools the X-ray tube are attached to the revolving body.

The X-ray tube has a housing. The X-ray tube has an X-ray radiation unit that radiates X-rays, and a circulation unit that is filled with cooling fluid and flows the cooling fluid to cool the X-ray radiation unit in the housing.

The cooler is arranged in the X-ray tube apparatus so as to improve the performance and efficiency of the X-ray tube apparatus. The cooler has another circulation unit that is different from the circulation unit of the X-ray tube. This other circulation unit is so formed as to deliver cooling fluid to the circulation unit of the X-ray tube, and cool down the cooling fluid which is taken in after circulating through the circulation unit, and deliver the cooling fluid to the circulation unit again.

The circulation unit and the other circulation unit are coupled by a coupler. The coupler has a plug that has its one end closed, and a socket that has its one end closed. The plug and the socket are coupled such that both the closed ends are coupled. Accordingly, both the one ends are opened, forming a flow path for cooling fluid. For example, the plug is coupled to the circulation unit of the X-ray tube, and the socket is coupled to the other circulation unit of the cooler.

The cooler may be set in environments in which the temperature changes when being transported. For example, the temperature changes between −25° C. and 70° C. Accordingly, the cooling fluid comes to be expanded and contracted. Furthermore, when using the X-ray tube apparatus, the temperature of the cooling fluid rises in order to cool down the X-ray radiation unit. Thus, the cooling fluid comes to be expanded.

When the cooling fluid is expanded, the cooling fluid may leak from coupling portions, etc., of components configuring the X-ray tube apparatus. When the cooling fluid leaks, air may infiltrate the circulation unit or another circulation unit from leakage portions. Furthermore, in the cooler, in case the cooling fluid is contracted, the closed state of one end of the socket is dissolved, and air may infiltrate the circulation unit from the socket. The X-ray absorption rate in the cooling fluid is different from that in air. Accordingly, air undesirably passes in front of X-rays radiated from the X-ray radiation unit, which prevents correct diagnosis.

BRIEF SUMMARY OF THE INVENTION

It is therefore an object of the present invention to overcome the above-mentioned drawbacks by providing a cooler that can absorb the expansion and contraction of cooling fluid due to the environmental temperature change, an X-ray tube apparatus having the cooler, and a method for operating the cooler.

To achieve the object, according to an aspect of the present invention, there is provided a cooler that circulates cooling fluid to cool down an X-ray tube, comprising:

a circulation unit that has a first end unit in which a delivery outlet to deliver the cooling fluid is formed, and a second end unit in which a take-in inlet is formed, and takes in the cooling fluid from the take-in inlet to cool down thus taken-in cooling fluid and deliver the cooling fluid to the delivery outlet; and an expansion mechanism that has a vessel which is attached to the circulation unit and which has an opening through which cooling fluid flowing in the circulation unit comes in and goes out, and a bellows that divides the inside of the vessel into a first chamber communicating with the opening and a second chamber;

the first end unit and the second end unit being detachably coupled to the X-ray tube, and being closed when being uncoupled from the X-ray tube, and the expansion mechanism capable of being switched between a first state in which coming in and going out of ambient atmosphere to and from the second chamber is shut off to restrict coming in and going out of the cooling fluid to and from the first chamber, and a second state in which coming in and going out of ambient atmosphere to and from the second chamber is released to allow coming in and going out of the cooling fluid to and from the first chamber.

According to another aspect of the present invention, there is also provided an X-ray tube apparatus, comprising:

an X-ray tube including an X-ray radiation unit that radiates an X-ray, a circulation unit that flows cooling fluid and cools down the X-ray radiation unit, and an expansion mechanism that has a vessel which is attached to the circulation unit and has an opening through which the cooling fluid flowing in the circulation unit comes in and goes out, and a bellows that divides the inside of the vessel into a first chamber communicating with the opening and a second chamber; and a cooler including another circulation unit that has a first end unit in which a delivery outlet to deliver the cooling fluid to the circulation unit is formed, and a second end unit in which a take-in inlet is formed, and takes in the cooling fluid delivered to the circulation unit from the take-in inlet to cool down thus taken-in cooling fluid and deliver the cooling fluid to the delivery outlet, and another expansion mechanism that has another vessel which is attached to the another circulation unit and has another opening through which the cooling fluid flowing in the another circulation unit comes in and goes out, and another bellows that divides the inside of the another vessel into another first chamber communicating with the another opening and another second chamber;

the circulation unit and the another circulation unit that has the first end unit and the second end unit being coupled to form a circulation path for the cooling fluid.

According to another aspect of the present invention, there is also provided a method for operating a cooler, comprising the steps of:

preparing a cooler that circulates cooling fluid to cool down an X-ray tube, and that includes a circulation unit that has a first end unit in which a delivery outlet to deliver the cooling fluid is formed, and a second end unit in which a take-in inlet is formed, and takes in the cooling fluid from the take-in inlet to cool down thus taken-in cooling fluid and deliver the cooling fluid to the delivery outlet, and an expansion mechanism that has a vessel which is attached to the circulation unit and which has an opening through which cooling fluid flowing in the circulation unit comes in and goes out, and a bellows that divides the inside of the vessel into a first chamber communicating with the opening and a second chamber, wherein the first end unit and the second end unit are detachably coupled to the X-ray tube, and are closed when being uncoupled from the X-ray tube; and switching between a first state in which coming in and going out of ambient atmosphere to and from the second chamber is shut off to restrict coming in and going out of the cooling fluid to and from the first chamber, and a second state in which coming in and going out of ambient atmosphere to and from the second chamber is released to allow coming in and going out of the cooling fluid to and from the first chamber.

According to still another aspect of the present invention, there is also provided a method for operating a cooler, comprising the steps of:

preparing a cooler that circulates cooling fluid to cool down an X-ray tube, and that includes a circulation unit that has a first end unit in which a delivery outlet to deliver the cooling fluid is formed, and a second end unit in which a take-in inlet is formed, and takes in the cooling fluid from the take-in inlet to cool down thus taken-in cooling fluid and deliver the cooling fluid to the delivery outlet, and an expansion mechanism that has a vessel which is attached to the circulation unit and which has an opening through which cooling fluid flowing in the circulation unit comes in and goes out as well as a vent through which ambient atmosphere comes in and goes out, and a bellows that divides the inside of the vessel into a first chamber communicating with the opening and a second chamber communicating with the vent, wherein the first end unit and the second end unit are detachably coupled to the X-ray tube, and are closed when being uncoupled from the X-ray tube; and switching between a first state in which the vent is closed to restrict coming in and going out of the cooling fluid to and from the first chamber, and a second state in which the vent is opened to allow coming in and going out of the cooling fluid to and from the first chamber.

Additional advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An X-ray tube apparatus and a method for operating a cooler of the X-ray tube apparatus according to an embodiment of the present invention will further be described below with reference to the accompanying drawings. In the embodiment, an X-ray CT apparatus as an X-ray tube apparatus, and a method for operating a cooler of the X-ray CT apparatus will be explained.

Figure 1:
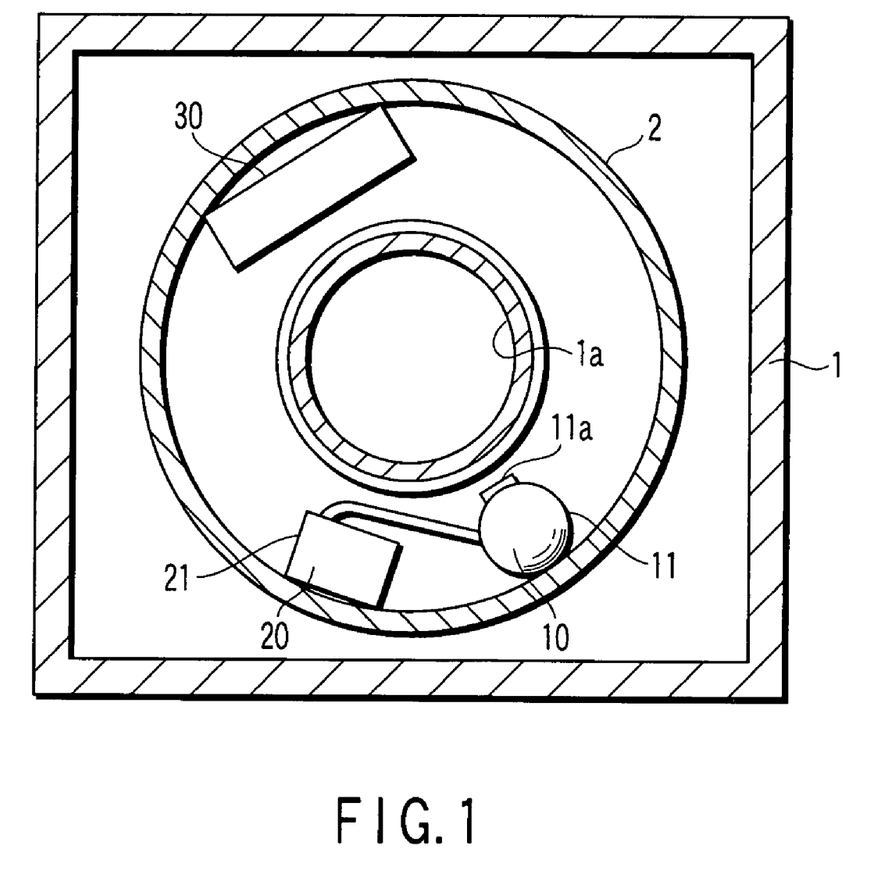
FIG. 1 shows a sectional view of an X-ray CT apparatus according to the embodiment of the present invention.
Figure 2:
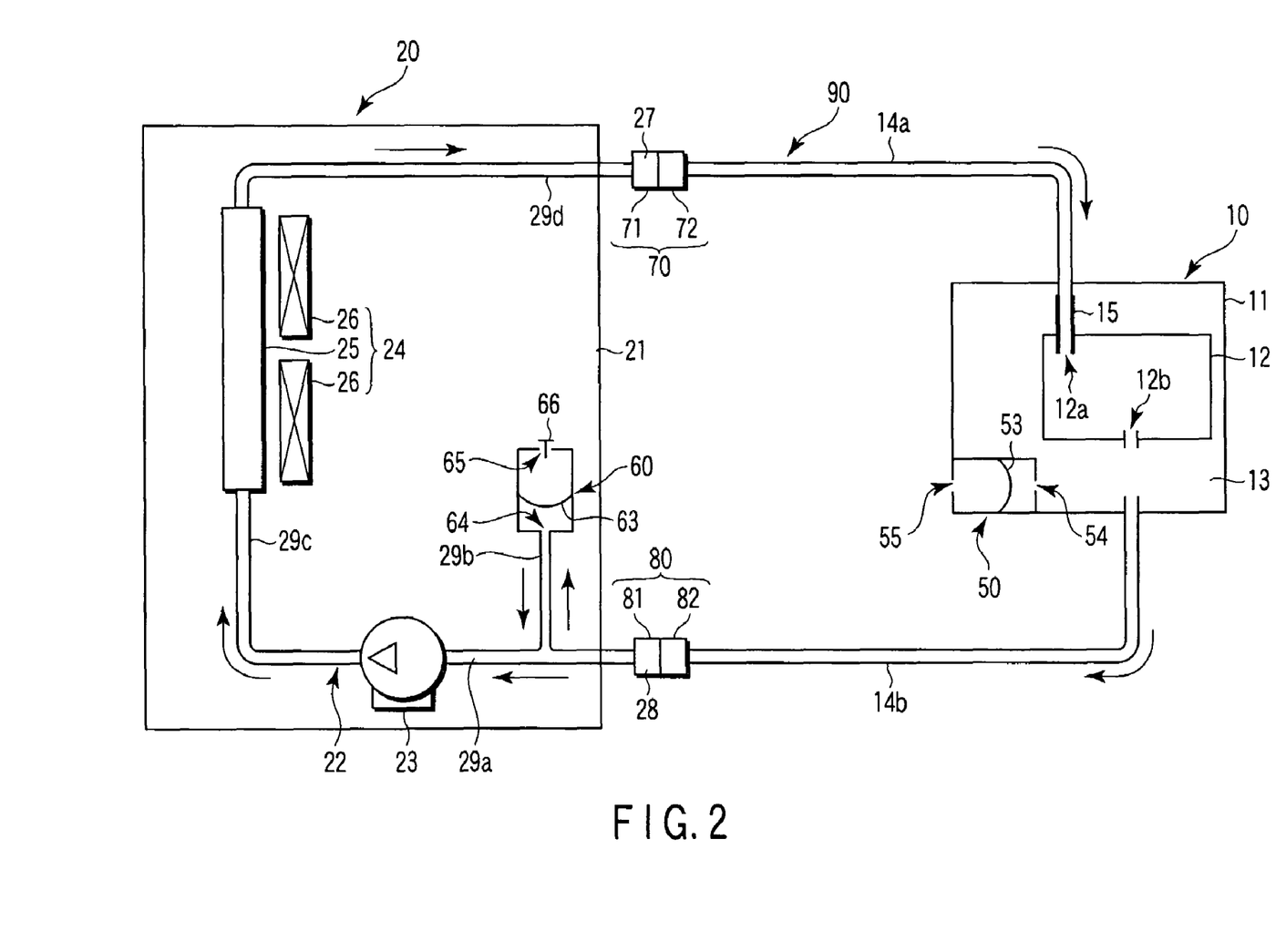
FIG. 2 shows a schematic view of an X-ray tube and a cooler which are shown in FIG. 1.

As shown in FIGS. 1 and 2, the X-ray CT apparatus has a pedestal 1, and the pedestal 1 has an introduction port 1a into which is introduce a target subject to be examined. On the pedestal 1, there is rotatably mounted a revolving body 2, which is so placed as to surround the introduction port 1a. The revolving body 2 has attached and fixed thereto an X-ray tube 10 that radiates X-rays, a cooler 20 that cools the X-ray tube 10, and an X-ray detection unit 30. The cooler 20 is so formed as to circulate cooling fluid so as to cool the X-ray tube 10.

The X-ray tube 10 and the cooler 20 are coupled by couplers 70, 80 working as coupling units. The coupler 70 has a plug 71 and a socket 72. The coupler 80 has a socket 81 and a plug 82.

The X-ray detection unit 30 is attached on the opposite side of the X-ray tube 10 when viewing from the introduction port 1a. In case of taking in an X-ray image of a target subject to be examined, the target subject is introduced into the introduction port 1a, and X-rays are radiated to the target subject by the X-ray tube 10, and the X-rays transmitted through the target subject are detected by the X-ray detection unit 30.

Next, the X-ray tube 10 and the cooler 20 will be explained in detail.

As shown in FIG. 2, the X-ray tube 10 includes a housing 11, an X-ray radiation unit 12 arranged in the housing 11, a circulation unit 13, and an expansion mechanism 50. The housing 11 has a housing window 11a. The housing 11 is filled with cooling fluid. The X-ray radiation unit 12 is so formed as to radiate X-rays, and the X-rays are radiated to the outside of the X-ray tube 10 through the housing window 11a.

The circulation unit 13 is so formed as to flow cooling fluid and cool down the X-ray radiation unit 12. The circulation unit 13 is formed to include area where the X-ray radiation unit 12 radiates X-rays. Furthermore, the X-ray tube 10 has the socket 72, a conduit tube 14a that couples the socket 72 and the circulation unit 13, the plug 82, and a conduit tube 14b that couples the plug 82 and the circulation unit 13.

In this embodiment, the X-ray radiation unit 12 has an inlet 12a that takes in cooling fluid, and an outlet 12b that discharges cooling fluid. The conduit tube 14a and the inlet 12a are coupled by a conduit tube 15. In this case, the circulation unit 13 includes the conduit tube 14a, the inside of the X-ray radiation unit 12, and the inside of the housing 11.

As can be seen from above, cooling fluid delivered from the conduit tube 14a is delivered to the inside of the X-ray radiation unit 12 through the conduit tube 15. Then, after cooling the X-ray radiation unit 12, the cooling fluid is discharged to the inside of the housing 11 from the outlet 12b to be delivered to the conduit tube 14b.

Figure 3:
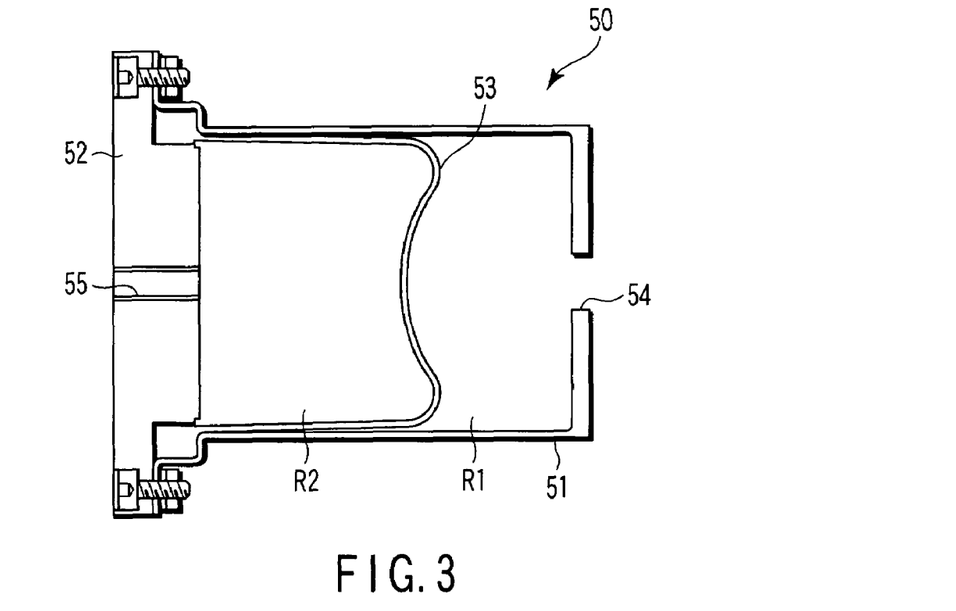
FIG. 3 shows an enlarged sectional view of an expansion mechanism of the X-ray tube.

As shown in FIGS. 2 and 3, the expansion mechanism 50 has a cylindrical vessel 51 that has its one end closed and has its other end closed by an end wall 52. The expansion mechanism 50 is attached to the circulation unit 13, and has an opening 54 through which cooling fluid flowing in the circulation unit 13 comes in and goes out, and a vent 55 through which air as ambient atmosphere comes in and goes out. The opening 54 is formed at one end of the vessel 51. The vent 55 is formed at the end wall 52, penetrating a part thereof.

The expansion mechanism 50 has a bellows 53 that divides the inside of the vessel 51 into a first chamber R1 communicating with the opening 54 and a second chamber R2 communicating with the vent 55. The bellows 53 is deformable. The vent 55 is opened at any time. Thus, the expansion mechanism 50 is so formed as to allow coming in and going out of cooling fluid to and from the first chamber R1 by releasing coming in and going out of air to and from the second chamber R2. Since the bellows 53 comes to be in the state in which the broadness and narrowness of the first chamber R1 and second chamber R2 can be changed, the expansion mechanism 50 can absorb the expansion and contraction of the cooling fluid. The expansion mechanism 50 accommodates volumetric changes in the coolant resulting from absorption of heat dissipated by the X-ray tube 10.

The cooler 20 includes a housing 21, a circulation unit 22 and an expansion mechanism 60 which are arranged in the housing 21. The circulation unit 22 includes a gear pump 23, and a cooling mechanism 24 having a radiator 25 and fans 26. The circulation unit 22 has a first end unit 27 in which an outlet to deliver cooling fluid to the circulation unit 13 of the X-ray tube 10 is formed, and a second end unit 28 in which an inlet to take in cooling fluid delivered to the circulation unit 13 is formed.

Furthermore, the circulation unit 22 includes the plug 71, socket 81, a conduit tube 29a coupling the socket 81 and the gear pump 23, a conduit tube 29b linked to the conduit tube 29a to couple the conduit tube 29a and the expansion mechanism 60, a conduit tube 29c coupling the gear pump 23 and the radiator 25, and a conduit tube 29d coupling the radiator 25 and the plug 71. In this embodiment, the plug 71 is the first end unit 27, and the socket 81 is the second end unit 28.

The gear pump 23 is so formed as to discharge cooling fluid delivered from the conduit tube 29a to the conduit tube 29c. The radiator 25 is so formed as to release heat of cooling fluid delivered from the conduit tube 29c, and the fans 26 are so formed as to send air to the radiator 25. Thus, the cooling mechanism 24 can cool the cooling fluid. Accordingly, the circulation unit 22 is so formed as to take in cooling fluid delivered to the circulation unit 13 from the second end unit 28, and cool thus taken in cooling fluid using the cooling mechanism 24 to deliver thus cooled cooling fluid to the first end unit 27.

Figure 4:
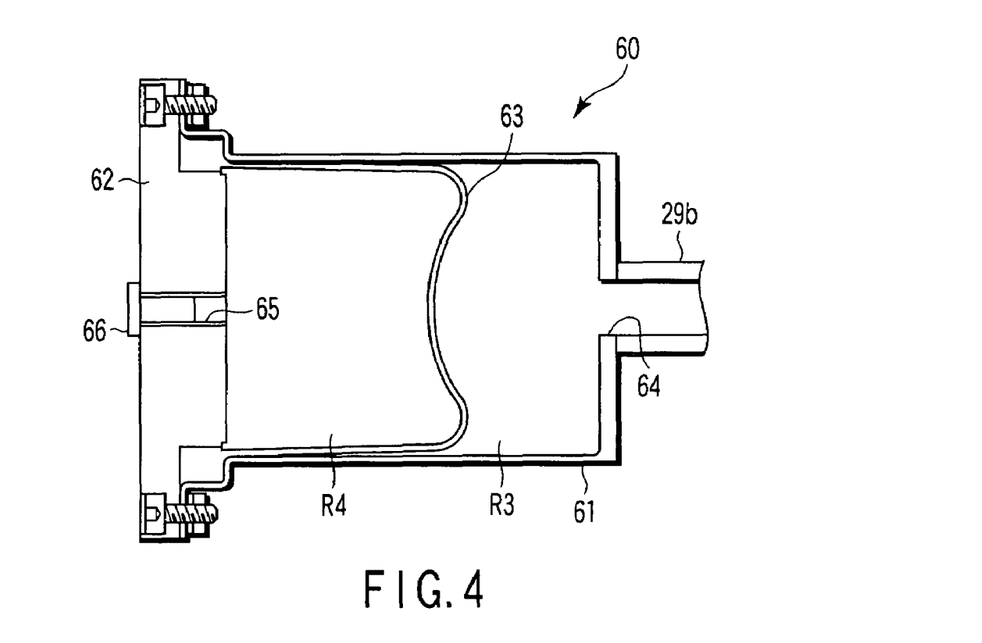
FIG. 4 shows an enlarged sectional view of an expansion mechanism of the cooler in a first state.
Figure 5:
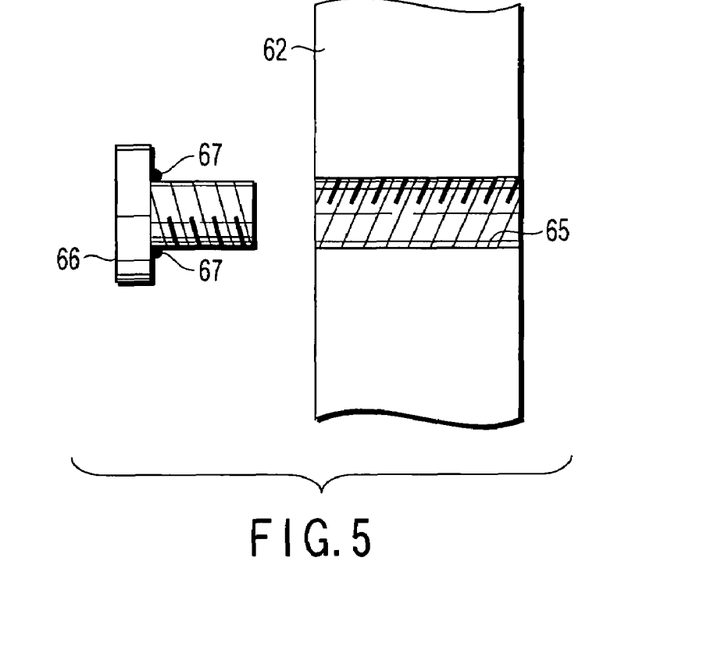
FIG. 5 shows an exploded sectional view of a part of the expansion mechanism shown in FIG. 4.

As shown in FIGS. 2, 4, and 5, the expansion mechanism 60 has a cylindrical vessel 61 that has its one end closed and has its other end closed by an end wall 62. The expansion mechanism 60 is attached to the circulation unit 22, and has an opening 64 through which cooling fluid flowing in the circulation unit 22 comes in and goes out, and a vent 65 through which air as ambient atmosphere comes in and goes out. The opening 64 is formed at one end of the vessel 61. The vent 65 is formed at the end wall 62, penetrating a part thereof.

The expansion mechanism 60 has a bellows 63 that divides the inside of the vessel 61 into a first chamber R3 communicating with the opening 64 and a second chamber R4 communicating with the vent 65. The bellows 63 is deformable. For example, the bellows 53 and the bellows 63 are made of rubber. The expansion mechanism 60 can be switched between a first state in which the X-ray tube 10 and the cooler 20 are coupled or in the coupled state, and coming in and going out of air to and from the second chamber R4 is shut off to restrict coming in and going out of cooling fluid to and from the first chamber R3, and a second state in which the X-ray tube 10 and the cooler 20 are not coupled, and coming in and going out of air to and from the second chamber R4 is released to allow coming in and going out of cooling fluid to and from the first chamber R3. In the second state, since the bellows 63 comes to be in the state in which the broadness and narrowness of the first chamber R3 and second chamber R4 can be changed, the expansion mechanism 60 can absorb the expansion and contraction of the cooling fluid. The expansion mechanism 60 accommodates volumetric changes in the coolant resulting from absorption of heat dissipated by the X-ray tube 10.

Figure 6:
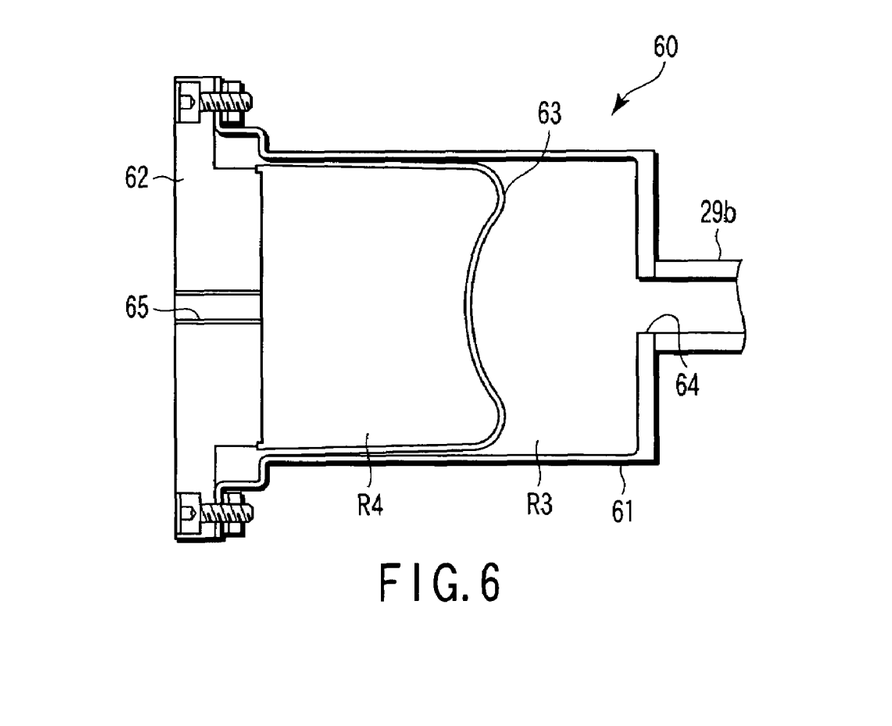
FIG. 6 shows an enlarged sectional view of the expansion mechanism of the cooler in a second state.

As shown in FIGS. 4, 5, and 6, in this embodiment, the expansion mechanism 60 is so formed as to close the vent 65 by fixing a cover member 66 in the first state, and open the vent 65 by taking off the cover member 66 in the second state. For example, the vent 65 is a screw hole, and the cover member 66 is a screw. The cover member 66 in the form of a screw has attached thereto an O-ring 67, which can close the vent 65 more tightly in the first state.

The circulation unit 13 of the X-ray tube 10 and the circulation unit 22 of the cooler 20 are coupled to form a circulation path 90 for cooling fluid. Specifically, the plug 71 and the socket 72 are coupled, and the socket 81 and the plug 82 are coupled, respectively.

The X-ray tube 10 and the cooler 20 are detachably formed. Specifically, the plug 71 and the socket 72 are detachably formed, and the socket 81 and the plug 82 are detachably formed, respectively. When the X-ray tube 10 and the cooler 20 are not coupled (second state), the plug 71, socket 72, socket 81, and plug 82 are closed, respectively.

According to thus configured X-ray CT apparatus, and the method for operating the cooler, the expansion mechanism 60 can be switched between the first state in which coming in and going out of air to and from the second chamber R4 is shut off to restrict coming in and going out of cooling fluid to and from the first chamber R3, and the second state in which coming in and going out of air to and from the second chamber R4 is released to allow coming in and going out of cooling fluid to and from the first chamber R3. Accordingly, being switched to the first state when the X-ray tube 10 and the cooler 20 are coupled or in the coupled state, and to the second state when the X-ray tube 10 and the cooler 20 are not coupled, respectively, the pressure inside the circulation path 90 can be kept at atmospheric pressure all the time.

The X-ray tube 10 has the expansion mechanism 50, and the cooler 20 has the expansion mechanism 60, respectively. Thus, the pressure inside the circulation path 90 can be kept at atmospheric pressure more securely. Furthermore, when the X-ray tube 10 and the cooler 20 are not coupled, the pressure inside the circulation unit 13 and the pressure inside the circulation unit 22 can be kept at atmospheric pressure, respectively.

Accordingly, even if cooling fluid comes to be expanded and contracted, the expansion and contraction can be absorbed by the expansion mechanism 50 and expansion mechanism 60, which can prevent the cooling fluid from leaking, and can prevent air from mingling the inside of the circulation path 90 (inside the circulation unit 13, inside the circulation unit 22). As described above, it becomes possible to provide the cooler that can absorb the expansion and contraction of cooling fluid due to the environmental temperature change, the X-ray CT apparatus having the cooler, and the method for operating the cooler.

When uncoupling the X-ray tube 10 and the cooler 20, since the expansion mechanism 60 is set in the first state, deviation of cooling fluid which is brought about when the cooling fluid comes into the first chamber R3 of the expansion mechanism 60 excessively after the uncoupling, that is, deviation of the cooling fluid between the X-ray tube 10 and the cooler 20 can be prevented.

This invention is not limited to the embodiment, but various modifications can be implemented without departing from the scope and spirit of the present invention. For example, the expansion mechanism 60 of the cooler 20 can be so formed as to open the vent 65 all the time to release coming in and going out of air to and from the second chamber R2 so as to allow coming in and going out of cooling fluid to and from the first chamber R1.

Figure 7:
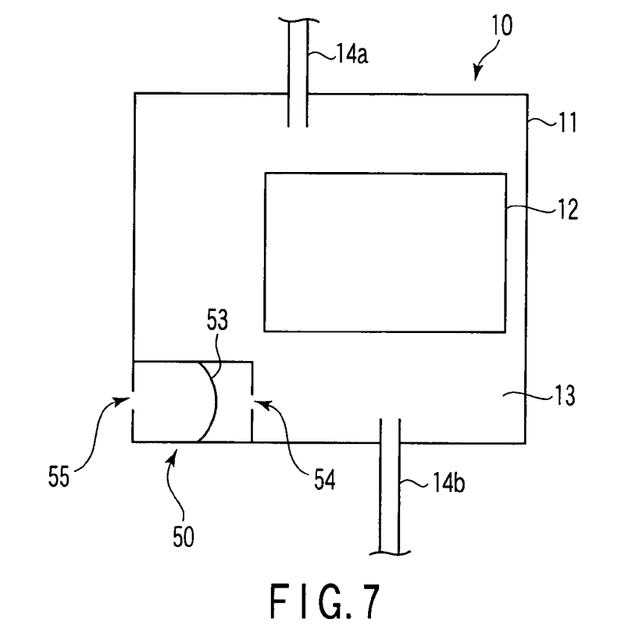
FIG. 7 shows a schematic sectional view of a modified example of the X-ray tube shown in FIG. 2.

As shown in FIG. 7, the X-ray radiation unit 12 does not have to have the inlet 12*a* and the outlet 12*b*. In this case, the circulation unit 13 is the inside of the housing 11. Therefore, cooling fluid sent from the conduit tube 14*a* is delivered to the inside of the housing 11. Then, the cooling fluid is delivered to the conduit tube 14*b* after cooling down the X-ray radiation unit 12.

Figure 8:
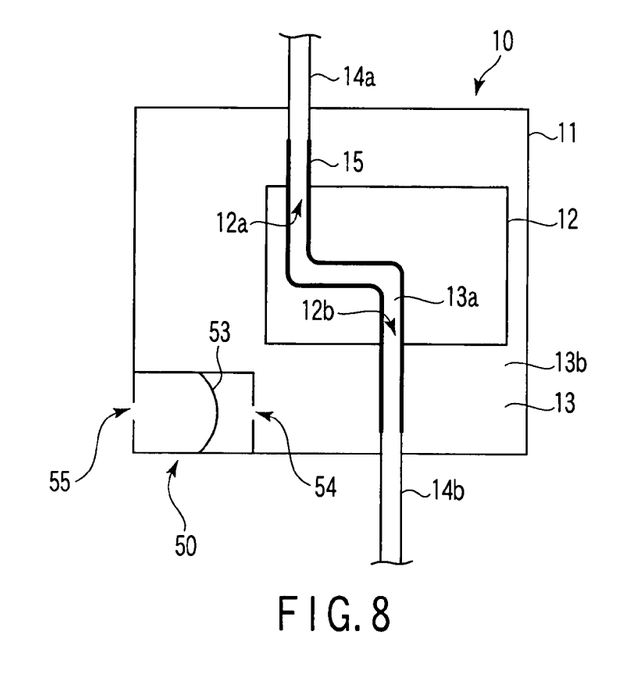
FIG. 8 shows a schematic sectional view of another modified example of the X-ray tube shown in FIG. 2.

As shown in FIG. 8, the conduit tube 15 may pass through the inside of the X-ray radiation unit 12, and have its one end coupled to the conduit tube 14*a* through the inlet 12*a*, while have its other end coupled to the conduit tube 14*b* through the outlet 12*b*. In this case, the circulation unit 13 has a first circulation unit 13*a* and a second circulation unit 12*b*. The first circulation unit 13*a* is the conduit tube 15. The second circulation unit 12*b* is the inside of the housing 11 which is filled with another cooling fluid, and the expansion mechanism 50 is attached to the second circulation unit 12*b*. Water and insulating oil may be used as the cooling fluid and other cooling fluid.

Accordingly, cooling fluid sent from the conduit tube 14*a* is delivered to the conduit tube 15. Then, the cooling fluid is delivered to the conduit tube 14*b* after cooling the X-ray radiation unit 12.

This invention is not restricted to the X-ray CT apparatus, and can be applied to an X-ray tube apparatus having the cooler.

What is claimed is:

1. A cooler that circulates cooling fluid to cool down an X-ray tube, comprising:

a circulation unit that has a first end unit in which an outlet to deliver the cooling fluid is formed, and a second end unit in which an inlet is formed, and takes in the cooling fluid from the inlet to cool thus taken-in cooling fluid and deliver the cooling fluid to the outlet; and an expansion mechanism that has a vessel which is attached to the circulation unit and which has an opening through which cooling fluid flowing in the circulation unit comes in and goes out, and a bellows that divides the inside of the vessel into a first chamber communicating with the opening and a second chamber;

wherein the first end unit and the second end unit being detachably coupled to the X-ray tube, and being closed when being uncoupled from the X-ray tube, and wherein the expansion mechanism is switched between a first state in which coming in and going out of ambient atmosphere to and from the second chamber is shut off to restrict coming in and going out of the cooling fluid to and from the first chamber, and a second state in which coming in and going out of ambient atmosphere to and from the second chamber is released to allow coming in and going out of the cooling fluid to and from the first chamber.

2. The cooler according to claim 1, wherein the vessel has a vent communicating with the second chamber, and the expansion mechanism is so formed as to close the vent in the first state, and open the vent in the second state.

3. An X-ray tube apparatus, comprising:

an X-ray tube including an X-ray radiation unit that radiates X-rays, a circulation unit that flows cooling fluid and cools the X-ray radiation unit, and an expansion mechanism that has a vessel which is attached to the circulation unit and which has an opening through which the cooling fluid flowing in the circulation unit comes in and goes out, and a bellows that divides the inside of the vessel into a first chamber communicating with the opening and a second chamber; and a cooler including another circulation unit that has a first end unit in which an outlet to deliver the cooling fluid to the circulation unit is formed, and a second end unit in which an inlet is formed, and takes in the cooling fluid delivered to the circulation unit from the inlet to cool thus taken-in cooling fluid and deliver the cooling fluid to the outlet, and another expansion mechanism that has another vessel which is attached to the other circulation unit and has another opening through which the cooling fluid flowing in the other circulation unit comes in and goes out, and another bellows that divides the inside of the another vessel into another first chamber communicating with the another opening and another second chamber;

wherein the circulation unit, and the first end unit and the second end unit being coupled to form a circulation path for the cooling fluid.

4. The X-ray tube apparatus according to claim 3, wherein the another expansion mechanism can be switched between a first state in which coming in and going out of ambient atmosphere to and from the other second chamber is shut off to restrict coming in and going out of the cooling fluid to and from the other first chamber, and a second state in which coming in and going out of ambient atmosphere to and from the other second chamber is released to allow coming in and going out of the cooling fluid to and from the other first chamber.

5. The X-ray tube apparatus according to claim 4, wherein the other vessel has a vent communicating with the other second chamber, and the other expansion mechanism is so formed as to close the vent in the first state, and open the vent in the second state.

6. A method for operating a cooler, comprising:

preparing a cooler that circulates cooling fluid to cool an X-ray tube, and that includes a circulation unit that has a first end unit in which an outlet to deliver the cooling fluid is formed, and a second end unit in which an inlet is formed, and takes in the cooling fluid from the inlet to cool thus taken-in cooling fluid and deliver the cooling fluid to the outlet, and an expansion mechanism that has a vessel which is attached to the circulation unit and which has an opening through which cooling fluid flowing in the circulation unit comes in and goes out, and a bellows that divides the inside of the vessel into a first chamber communicating with the opening and a second chamber, wherein the first end unit and the second end unit are detachably coupled to the X-ray tube, and are closed when being uncoupled from the X-ray tube; and switching between a first state in which coming in and going out of ambient atmosphere to and from the second chamber is shut off to restrict coming in and going out of the cooling fluid to and from the first chamber, and a second state in which coming in and going out of ambient atmosphere to and from the second chamber is released to allow coming in and going out of the cooling fluid to and from the first chamber.

7. A method for operating a cooler, comprising:

preparing a cooler that circulates cooling fluid to cool an X-ray tube, and that includes a circulation unit that has a first end unit in which an outlet to deliver the cooling fluid is formed, and a second end unit in which an inlet is formed, and takes in the cooling fluid from the inlet to cool thus taken-in cooling fluid and deliver the cooling fluid to the outlet, and an expansion mechanism that has a vessel which is attached to the circulation unit and which has an opening through which cooling fluid flowing in the circulation unit comes in and goes out as well as a vent through which ambient atmosphere comes in and goes out, and a bellows that divides the inside of the vessel into a first chamber communicating with the opening and a second chamber communicating with the vent, wherein the first end unit and the second end unit are detachably coupled to the X-ray tube, and are closed when being uncoupled from the X-ray tube; and switching between a first state in which the vent is closed to restrict coming in and going out of the cooling fluid to and from the first chamber, and a second state in which the vent is opened to allow coming in and going out of the cooling fluid to and from the first chamber.

* * * * *